United States Patent
Gaukel

(12) 
(10) Patent No.: US 6,337,665 B1
(45) Date of Patent: Jan. 8, 2002

(54) ANTENNA ORIENTATION MAINTAINING SYSTEM IN A SYSTEM FOR TRACKING INDIVIDUALS, AND METHOD OF USE

(75) Inventor: John J. Gaukel, Elkhorn, NE (US)

(73) Assignee: Advanced Business Sciences, Inc., Omaha, NE (US)

(*) Notice: Subject to any disclaimer, the term of this patent is extended or adjusted under 35 U.S.C. 154(b) by 0 days.

(21) Appl. No.: 09/690,553

(22) Filed: Oct. 18, 2000

Related U.S. Application Data

(63) Continuation-in-part of application No. 09/312,708, filed on May 17, 1999, now abandoned, which is a continuation-in-part of application No. 08/840,057, filed on Apr. 24, 1997, now Pat. No. 6,072,396.
(60) Provisional application No. 60/087,727, filed on Jun. 2, 1998.

(51) Int. Cl.[7] .................................................. H04B 1/38
(52) U.S. Cl. ........................ 343/765; 455/575; 343/718
(58) Field of Search .................................. 343/702, 718, 343/765, 882, 880; 455/575, 90, 100

(56) References Cited

U.S. PATENT DOCUMENTS

| | | | | |
|---|---|---|---|---|
| 5,512,912 A | * | 4/1996 | Ross et al. | 343/765 |
| 5,523,766 A | * | 6/1996 | Erceg | 343/702 |
| 5,884,198 A | * | 3/1999 | Kese et al. | 455/575 |

* cited by examiner

*Primary Examiner*—Don Wong
*Assistant Examiner*—James Clinger
(74) *Attorney, Agent, or Firm*—James D. Welch

(57) ABSTRACT

Disclosed is a gimbaled antenna system mounting system for maintaining an electromagnetic signal reception means, of an antenna system present in a remote unit in a global positioning system (GPS) based system for continuous electronic monitoring and tracking of monitored individual(s) from a central control station (CCS), in an essentially constant desired orientation with respect to an earth orbiting satellite source of electromagnetic signals, when, in use, change occurs in the orientation of a structural frame element of the remote unit to which the antenna system is, via the gimbaled antenna system mounting system, mounted.

16 Claims, 4 Drawing Sheets

US 6,337,665 B1

ANTENNA ORIENTATION MAINTAINING SYSTEM IN A SYSTEM FOR TRACKING INDIVIDUALS, AND METHOD OF USE

This Application is a continuation in part Ser. No. 09/312,708 filed May 17, 1999 now abandoned, and via said 708 Application, Provisional Application Ser. No. 60/087,727 filed Jun. 2, 1998, which is a CIP application Ser. No. 08/840,057 filed Apr. 24, 1997, which is now U.S. Pat. No. 6,072,396.

TECHNICAL FIELD

The present invention relates to personnel tracking systems and methods generally, and more particularly to a gimbal mounted antenna system orientation maintaining system in remote units of a central control station monitored personnel tracking system, which remote units utilize satellite global positioning. In use, the present invention maintains an electromagnetic signal reception means of an antenna system therein in an essentially constant electromagnetic signal reception orientation with respect to at least one earth orbiting satellite, when the orientation of a structural frame "bag" element of a personnel tracking system remote unit, which contains the gimbal mounted antenna system, is changed.

BACKGROUND

It is well known that the orientation of an antenna system with respect to a transmission source of electromagnetic signals is critical to the capability of said antenna system to provide high quality reception of electromagnetic signals transmitted by said transmission source. For instance, a terrestrial based antenna system must have electromagnetic signal reception elements thereof oriented properly to receive electromagnetic signal transmission from an earth orbiting satellite. A non-limiting example of a system wherein orientation of electromagnetic signal reception elements of an antenna system with respect to an earth orbiting satellite is important to the operation thereof, is described in U.S. Pat. Nos. 5,072,396 and 6,100,806, which are incorporated by reference into this Disclosure as are applications Ser. Nos. 09/312,708, and 60/087,727. Said incorporated Patents describe statically mounted electromagnetic signal receiving antenna systems and the applications introduce gimbal mounting thereof.

Additional known Patents which are relevant to personnel tracking systems include a Patent to Kotoh, U.S. Pat. No. 4,673,936. Said 936 Patent describes a rescue transmitter apparatus which is adapted to be worn on a person's wrist. Said transmitter apparatus sends a microwave signal which, in use, is received by a search and rescue craft thereby allowing relative, but not absolute, positioning of the transmitter apparatus, by use of a directional antenna. A Patent to Damell et al., U.S. Pat. No. 5,043,736 describes a hand-held apparatus which contains a Global Positioning System (GPS), which allows determining an absolute, (ie. longitude and lattitude), and a cellular telephone transmitter.

Several Patents have been proposed in the field of prisoner monitoring in house arrest scenarios. One is described in a Patent to Pauley et al., U.S. Pat. No. 4,885,571, wherein a "tag" device, which is worn by a prisoner, periodically is caused to transmit to a field unit. Receipt of the signal at a field unit is an indication that the "tag" is within a transmission range, but no absolute, or even relative, positioning data is made available. Another Patent, U.S. Pat. No. 5,493,694, describes a central station system which is used to send interrogation signals to a fleet of vehicles requesting that selected vehicles respond, which central station system then waits and listens for a response. The central station can also receive signals indicating that a fleet vehicle requires assistance, then respond with a signal which provides location information to other fleet vehicles, certain of which, if within a predetermined distance to the vehicle which requires assistance, can respond. U.S. Pat. No. 5,528,248 to Steiner et al., describes a hand-held personal digital location apparatus which has a (GPS) antenna and receiver which serves to provide location information, however, no mention of application to continuous tracking and monitoring of an individual is mentioned. U.S. Pat. No. 5,541,845 to Klein describes methods for monitoring adherence of a vehicle to prescribed planned route and/or time schedule. The vehicle can utilize a (CPS), or other location determining system. Said 845 Patent provides that Non-adherence to a specified route or time schedule causes the vehicle to send a signal to a central station. U.S. Pat. No. 5,552,772 to Janky et al., describes a location determination system used to determine the present location of a firefighter at a fire site or the like. One embodiment provides that a firefighter carry a unit that receives a signal from a group of sources. A central station interrogates the one or more of said units, which each respond with location information. While the system can store information, the remote units do not have processors which can store location information data or upload or download information showing past locations. U.S. Pat. No. 5,568,119 to Schipper et al., discloses a method and apparatus which is applicable to use in house-arrest settings, and allows monitoring the current location of a remote unit, which can be checked at selected times. An arrestee wears a location determining device which can combine with a (GPS) type system or ground based system. Either the remote unit or central station can be used to process information and the central station compares said location with prescribed boundaries to determine if the arrestee is staying therewithin. If an expected location determining signal is not received, or a received signal indicates that an arrestee has strayed outside allowed boundaries, the central station notifies appropriate authorities. The remote unit can include tamper detection equipment, and optionally, the remote unit can transmit position information in encrypted form. The 119 invention provides for periodic modification of allowed time scheduled arrestee positioning. A Patent to Hoshen, U.S. Pat. No. 5,461,390 describes a locator device which can be useful in house arrest and stalker detection. The device utilizes a polling type apparatus wherein a polling message is sent from a central unit to remote units. There is no provision for "real-time" detection of violations, or of any capability to upload or download data. U.S. Pat. No. 5,416,695 to Stutman et al., describes a method and apparatus for alerting patients and medical personnel of emergency medical situations. A telephone network is utilized to transmit information from a patient, and a (GPS) remote telemetry device also collects information for transmission to a host computer. When patient parameters exceed set ranges, an alarm is sounded. A "panic-button" is also provided which permits the patient to directly contact the host computer. A Patent to Baumann, No. U.S. Pat. No. 5,416,468 describes a plurality of individual remote units on persons, which transmit location data to a "field unit" at periodic intervals. If information is not received within a predetermined time range, an alarm may be triggered. The remote units can include "detectors" which sense environmental conditions and transmit said data along with location data. The Baumann remote units can only transmit data and do not have the capability to determine if it is received by the field unit, and the remote units do not store tracked information.

U.S. Pat. Nos. 4,682,155 and 5,268,670 to Shirley and Brasch et al., which focus on monitoring the movements of medical patients, are also known and disclosed.

Patents particularly relevant to the present invention antenna orientation system in a personnel tracking system, and a method of use for maintaining an electromagnetic signal reception means of an antenna system therein in an essentially constant desired orientation with respect to an electromagnetic signal transmission source, when the orientation of a structural frame element of said personnel tracking system is changed were also identified. Perhaps the most relevant is a Patent to Friedrich et al., U.S. Pat. No. 5,410,325 which describes an antenna assembly which is free to rotate about at least one axis parallel to the axis of rotation of an elevationally moveable dump truck bed. Another Patent, U.S. Pat. No. 5,512,912 to Ross et al., particularly in FIG. 4 thereof, provides a two axis gimbaled mounting which allows an antenna to maintain a predetermined position despite the influence of externally applied accelerations, including effecting satellite orientation. A chamber holds a damping fluid which serves in damping oscillations. U.S. Pat. No. 1,569,325 to Leib, describes a radio direction finder comprising a frame-ship antenna and a spherically curved antenna which mounts to a support. The radio direction finder further comprises a counter-weight below the support such that the axis can swing laterally in all directions and assume a vertical position regardless of the inclination of the support. U.S. Pat. No. 5,670,967 to Sarjala describes a method and system for mechanical stabilization wherein a body is supported at its center of mass, whereby no acceleration in any direction causes a torque induced by the inertial force. The body maintains its position in relation to the earth gravity field, even if accelerations and various kenetic states are applied at the point of support. A Patent to Gordon et al., U.S. Pat. No. 5,489,911 describes an antenna for use in Marine VHF Systems which includes a gimbaled device. U.S. Pat. No. 5,111,212 to DeSatnick et al. describes a radar antenna mount in which the antenna is mounted with its center of gravity below the pivot axis. Viscous damping is also provided to prevent uncontrolled swinging of the antenna. U.S. Pat. 986,806 to D'Antonio describes a reflector for a wireless antenna that is mounted via a bearing socket and a ball journal, such that the reflector is on one side of the bearing socket and a ball journal via a stem, and a counter weight is present on the opposite side of said stem. U.S. Pat. No. 4,920,350 to McGuire et al is disclosed as it describes a casing, a stage and an antenna mounted on the stage. Additionally disclosed for general purposes is U.S. Pat. No. 5,943,027 to Thill et al.

As mentioned, recently Issued Patents to the same Inventor which are disclosed for relevant background are U.S. Pat. Nos. 6,072,396 and 6,100,806.

Even in view of the prior art, there remains need for a system for continuous electronic monitoring and tracking of individual(s) at remote unit location(s) from a central control station (CCS), where each said remote unit comprises a global positioning system (GPS) with an antenna affixed thereto via a gimbaled stage means, such that the changing of the orientation of a remote unit antenna system electromagnetic signal reception means in use, does not cause said antenna system electromagnetic signal reception means to become oriented so that it does not receive position determining signal(s) from one or more earth orbiting satellites.

DISCLOSURE OF THE INVENTION

The present invention is a system for continuous electronic monitoring and tracking of monitored individual(s) from a central control station (CCS), and can be described as comprising one or more remote unit(s) (RU), each of which remote unit(s) (RU) contain geographic position determining means for determining the position thereof at determined time(s). Each remote unit (RU) has therein a programmable central processing unit (CPU) with accompanying memory storage which is connected to the position determining means, said combination having the capability to store determined position signals in combination with a generated time stamp. Said system for continuous electronic monitoring and tracking of monitored individual remote unit(s) each further comprise communication means connected to the programmable central processing unit (CPU) which enable transmitting data from the remote unit (RU) to the central control station (CCS). Said communication means further enable receiving data from the central control station (CCS) and providing said data to the central processing unit (CPU). The central processing unit (CPU) is programmed to accumulate time stamped remote unit (RU) position signal data at determined time intervals and transmit said accumulated position signal and time stamped data to the central control station (CCS) via a downlink. It is a critical element of the present invention system for continuous electronic monitoring and tracking of monitored individuals, that while communication means for receiving data from a present invention remote unit (RU) can be land based or utilize satellite links etc., the position determining means are of the type which receive electromagnetic radiation from at least one earth orbiting satellite, (ie. that is the position determining means constitute a global positioning system (GPS)).

It is further disclosed that a present invention system for continuous electronic monitoring and tracking of monitored individuals remote unit (RU) comprises an element worn on the body, (eg. typically on the wrist or ankle), of a monitored individual who's position is to be tracked. Said element which is worn on the body on a monitored individual, in use, communicates with a nearby positioned "bag". It is the nearby positioned "bag" that contains the majority of the just described remote unit (RU) elements, (eg. (CPU), memory etc.), including the (GPS) antenna system which is mounted thereto via the present invention gimbaled stage. It is to be understood that while cable has been demonstrated as a particularly functional means, said communication between said body worn element and said "bag" can be via any functional means, (eg. cable, fiber optics, ultrasound or electromagnetic transmission through a space etc.).

The present invention is specifically found in the combination of:
- a remote unit of a system for continuous electronic monitoring and tracking of monitored individuals, which, as described, contains a global positioning system (GPA) antenna system which comprises electromagnetic signal receiving means; and
- a gimbal mounted, (ie. gimbaled), antenna system mounting means, (eg. stage), which serves to mount said antenna system to a present invention remote unit "bag" structural frame element such that in use said gimbaled stage operates to maintain said electromagnetic signal receiving means oriented so as to receive electromagnetic signals from at least one earth orbiting satellite, when the "Bag" structural frame is caused to change orientation.

It is to be understood that the preferred present invention gimbaled stage is affixed to an upper end of an elongated arm which has a counter-weight affixed to a lower end thereof, and said elongated arm is pivotally mounted to a present invention "bag" structural frame element, at a point between said gimbaled stage and counter-weight. Functionally, the benefit of the present invention is found in the fact that said present invention "bag" structural frame element can be rotated in an effective pendulum plane of said present invention elongated arm, without affecting an essentially constant orientation of said present invention antenna system electromagnetic signal reception means present on said invention gimbaled stage, with respect to an electromagnetic signal transmission means, (eg. an orbiting satellite).

The present invention then enables, via the gimbaled antenna system mounting, the maintaining of the orientation of a (GPS) antenna system electromagnetic signal receiving means essentially constant, and appropriate to receive electromagnetic signals from at least one satellite orbiting the earth, even when a "bag" containing said (GPS) antenna system is caused to be tipped so as to be positioned in various positions. Such "tipping" can occur where, for instance, a "bag" is knocked-over onto its side.

Continuing, a method of keeping electromagnetic signal receiving means of an antenna system oriented so as to receive signals from a source of electromagnetic signals, as applied to a system for continuous electronic monitoring and tracking of monitored individuals, comprises the steps of:

a. providing an antenna system in a system for continuous electronic monitoring and tracking of monitored individuals comprising electromagnetic signal receiving means affixed to a gimbaled stage, said gimbaled stage being affixed to an upper end of an elongated arm which has a counter-weight affixed to a lower end thereof, said elongated arm being pivotally mounted to a "bag" structural frame element, such that said "bag" structural frame element can be rotated in an effective pendulum plane of said elongated arm without affecting an essentially constant orientation of said antenna system electromagnetic signal reception means;

b. orienting said antenna system electromagnetic signal receiving means appropriately to receive electromagnetic signals from said source of electromagnetic signals;

c. causing said "bag" structural frame element to rotate in an effective pendulum plane of said elongated arm;

such that said counter-weight affixed to the lower end of said elongated arm is continuously attracted by gravity toward the earth with the result that, via rotation of said elongated arm about said pivotal mounting to said "bag" structural frame element with respect to said "bag" structural frame element, the orientation of said antenna system electromagnetic signal receiving means present on the said gimbaled stage remains essentially constant while said "bag" structural frame element is caused to be so rotated.

It is specifically disclosed that an effective "pendulum plane" of said elongated arm can be essentially three-dimensional, and is not limited to a fixed two-dimensional plane as referenced to said "bag" structural frame element.

It is further noted that practice of the present invention method of maintaining the orientation of an antenna system electromagnetic signal receiving means appropriate to receive electromagnetic signals from an orbiting earth satellite, can involve practice with a variety of types of antenna systems. For instance, the present invention can be applied to continuously maintain an essentially flat patch antenna system electromagnetic signal reception surface means in a plane which is essentially orthogonal to the vector direction of the force of gravity. As well, the present invention can be applied to continuously maintain an elongated dimension projection direction of a whip or helical antenna system electromagnetic signal reception means oriented essentially parallel to the vector direction of the force of gravity or, alternatively stated, along a radius which projects from the center of the earth outward toward the position of an electromagnetic signal transmitting earth orbiting satellite, said radius intersecting the surface of an idealized spherical model of the earth at a ninety degree angle.

While a present invention "bag" has been described in prior co-pending parent patent applications by the inventor, (eg. Ser. Nos. 08/840,057 and 08/367,057), and while gimbaled stage mounting of antenna systems to structural frames are independently known, no known reference describes a system for continuous electronic monitoring and tracking of monitored individuals comprising a global positioning system (GPS) electromagnetic signal receiving means affixed to a gimbaled stage, and method of use, as described herein. Said combination provides particular benefit in situations wherein a present invention "bag" is prone to being knocked-over in use.

The present invention will be better understood by reference to the Detailed Description Section of this Disclosure, in combination with the Drawings.

SUMMARY

It is therefore a primary purpose of the present invention to provide a gimbal mounted antenna system in remote unit(s) of a system for continuous electronic monitoring and tracking of monitored individual(s) from a central control station.

DETAILED DESCRIPTION

Figure 1A:
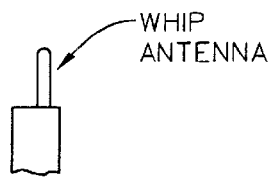
FIG. 1A shows a whip-type antenna.
Figure 1B:
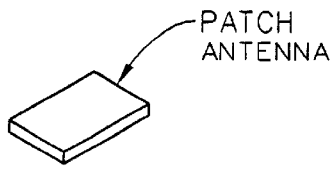
FIG. 1B shows a patch-type antenna.
Figure 1C:
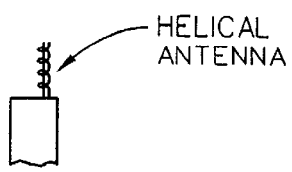
FIG. 1C shows a helical-type antenna.

Turning generally now to the Drawings, it is to be appreciated that the present invention (PI) includes a system for maintaining the orientation of electromagnetic signal reception means in an antenna system (A) oriented, (eg. "faced" or "directed"), so that said antenna system (A) can receive electromagnetic signals from a source of electromagnetic signals, (eg. an earth orbiting satellite). Where a "Patch" antenna system, as shown in FIG. 1B, is present, the action of the present invention can be described as:

continuously maintaining an essentially flat antenna system electromagnetic signal reception surface means in a plane which is essentially orthogonal to the vector direction of the force of gravity.

Where a "Whip" antenna system as shown in FIG. 1A, or "Helical" antenna as shown in FIG. 1C, is present, the action of the present invention can be described as:

continuously maintaining an elongated dimension projection direction of said antenna system electromagnetic signal reception means oriented essentially parallel to the vector direction of the force of gravity or, alternatively stated, along a radius which projects from the center of the earth outward toward the position of an electromagnetic signal transmitting earth orbiting satellite, said radius intersecting the surface of an idealized spherical model of the earth at a ninety degree angle.

Turning now to FIGS. 2A, 2B, 3A, 3b and 4, the present invention system (PI) can be best described as comprising at least one structural frame element (FE1) (FE2) (FE3) to which is pivotally mounted, an elongated arm (EA). (Note that multiple structural frame elements (FE1), (FE2) and (FE3) are demonstrated in FIG. 4 with three present invention systems (PI1), (PI2) and (PI3) indicated as present and affixed to structural frame elements (FE1), (FE2) and (FE3) respectively).

Referring specifically to FIGS. 2A, 2B, 3A and 3B, it should be understood that an elongated arm (EA) of a present invention system further comprises a counter-weight (W) present at some downward projected distance (L) below, (ie. toward the surface of the earth), the location of the pivotal mounting (P) of said elongate arm (EA) to said to said least one structural frame element, (eq. FE1), so that, as viewed in frontal elevation in FIGS. 3A and 3B, a "pendulum-like" system is functionally effected in which elongated arm (EA) can swing in an effective "pendulum plane", (see FIGS. 3A and 3B where the effective "pendulum plane" is in the surface plane of the paper. For comparison, it is noted that the effective "pendulum plane" of (PI3), as oriented in the Top View of FIG. 4, would be into the surface plane of the paper).

Figure 2A:
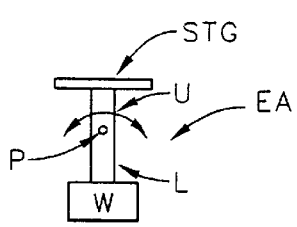
FIGS. 2A and 2B demonstrate the basic elements of the present invention system for one and three dimensional gimbaling.
Figure 2B:
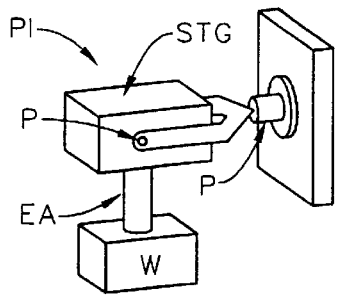

Additionally, FIGS. 2A and 2B show that a present elongated arm (EA) further comprises an antenna system mounting means, (ie. stage (STG)), present at some upward projected distance (U) above, (similarly viewed in frontal elevation in FIGS. 3A and 3B), said pivotal mounting (P). It is noted that, typically, for an elongated arm (EA), the downward projected distance (L) is greater than the upward projected distance (U), and that it's effective "pendulum plane" is a plane in which said elongated arm (EA) can rotate about its pivotal mounting (P) to a structural frame element, (eg. (FE1) in FIGS. 3A and 3B).

Figure 3A:
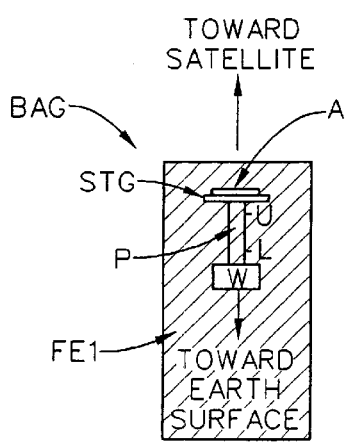
FIG. 3A shows a front elevational view of a present invention remote unit system gimbaled stage affixed to a "bag" structural frame element.
Figure 3B:
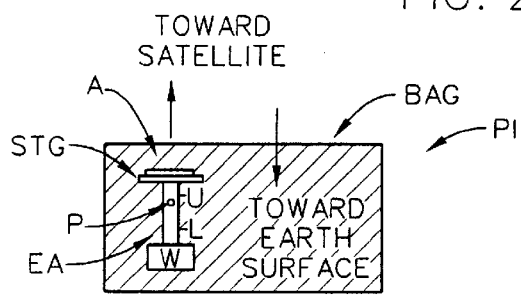
FIG. 3B shows a front elevational view of the present invention of FIG. 3A affixed to the structural frame element of FIG. 3A, with said "bag" structural frame element having been rotated ninety degrees from the position thereof shown in FIG. 3A.

Functionally, in use, a present invention system (PI) serves to keep electromagnetic signal receiving means of an antenna system (A) mounted to the antenna system mounting means (STG) thereof, "faced" or "projected" upwardly when the structural frame element, (eg. FE1), to which said elongated arm (EA) is pivotally affixed is caused to rotate in the effective "pendulum plane" of said elongated arm (EA). FIGS. 3A and 3B demonstrate the functional action of a present invention system (PI). FIG. 3A shows a front elevational view of a present invention system (PI) affixed to a structural frame element (FE1). FIG. 3B shows a front elevational view of the present invention (PI) of FIG. 3A affixed to the structural frame element (FE1), with said structural frame element (FE1) having been rotated ninety degrees counterclockwise from the position thereof shown in FIG. 3A. Note, however, that the FIG. 3B orientation of antenna system (A) shown present on stage (STG), is not changed from that shown in FIG. 3A, and that said counterweight (W) is constant in its orientation below said pivotal mounting (P) of said elongated arm (EA), to said structural frame element (FE). This is the necessary result of the attraction of gravity on the counter-weight (W) present at a projected distance (L) below the location of the pivotal mounting (P) of said elongated arm (EA) to said to said structural frame element, (eg. FE1).

Figure 4:
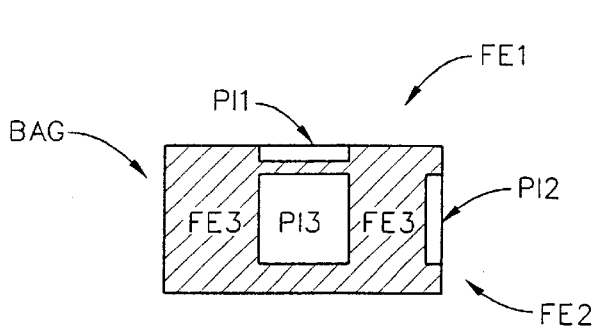
FIG. 4 shows a Top view of a box in which are mounted three gimbaled stage systems, each with a different effective "pendulum plane".

As alluded to, FIG. 4 shows, in a Top View, that multiple present inventions, (eg. (PI1) and (PI2)), systems can be present, each with a different effective "pendulum plane". For instance, where it is desired to monitor deviation from an upright condition of a four sided box (BAG), (which appears rectangular or square in top view), said two present invention systems (PI1) and (PI2) can be utilized. One present invention system (PI1) can be mounted to a back (FE1) structural frame element, (also shown as viewed in frontal elevation in FIGS. 3A and 3B), of said four sided box, and one said present invention system (PI2) can be mounted to a right side (FE2) structural frame element thereof. Where the present invention is not present, "tipping" or "rotation" (eg. the knocking over), of said four sided box (BAG) around an axis perpendicular to either the front or back of said four sided box, or around an axis perpendicular to the left and right sides thereof, will necessarily cause electromagentic signal receiving means of an antenna system affixed to the four sided box (BAG) to undesirably re-orient antenna system (A) electromagnetic signal receiving means. As demonstrated in FIGS. 3A and 3B, however, with the present invention system in place, said "tipping" or "rotation" (eg. the knocking over), of said four sided box (BAG) in the effective "pendulum plane" of present invention (PI1) will not cause the electromagnetic signal receiving means of an affixed antenna system (A) to deviate from its "upward" facing" orientation. FIGS. 3B shows a Front View of a (BAG) which has been rotated in the effective "pendulum plane" of present invention (PI1), ninety degrees from the position shown in FIG. 3A. Again, note that FIG. 4 shows present invention (PI1) as represented in FIGS. 3A and 3B, but from a Top View. A similar recitation would apply regarding present invention (PI2) shown in said FIG. 4, with respect to the appropriate effective "pendulum plane" thereof. While perhaps not as important as (PI1) and (PI2), FIG. 4 also shows a third present invention (PI3) can be present on the bottom, (FE3), structural frame element of said four sided box (BAG). Present invention (PI3), of course, allows compensation for rotation of said (BAG) around a third axis which is perpendicular to the page, as shown. Present invention (PI3) would provide additional electromagnetic signal receiving means appropriately oriented, where a (BAG) is tipped-over onto a side thereof.

Figure 5:
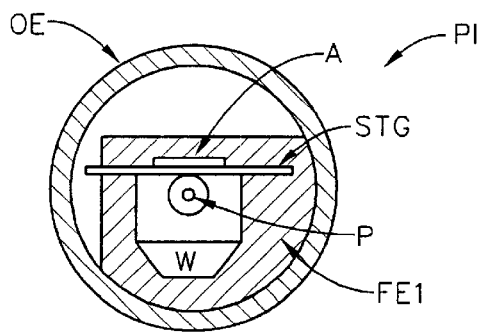
FIG. 5 shows a front elevational view of a practical embodiment of the present invention system showing an outer enclosure.

FIG. 5 shows a front elevational view of a practical embodiment of the present invention (PI) system showing an outer essentially tubular shaped enclosure (OE). The identifiers in FIG. 5 are otherwise the same as utilized in FIGS. 2A, 3A and 3B.

It is noted that the pivot means (P) can be of various types, (eg. brass rod, jewel-type, bearing-type, air-bearing-type, bushing-type, wire-torsion-type etc).

It is also noted that the terminology "antenna system" is used as it is possible for an antenna to be comprised of more than simply an electromagnetic signal reception means. For instance, an "antenna system" can include active electronic amplification means and can even include an entire electronic signal receiver means. A benefit results from placing active elements of an antenna system on the stage (STG), in that other than relatively "stiff", (in torsion), coaxial cable can be utilized to carry signal therefrom, with the benefit that being that rotation of the present invention (PI) elongated arm (EA) about the pivotal mounting (P) is less hindered in use by said more flexible wire.

It is further noted that the present invention (PI) can be considered to provide a "gimbaled stage" in that ideally the antenna system mounting means is a stage (STG) which is affixed to an upper end of an elongated arm (EA), which stage (STG) remains essentially horizontally oriented regardless of the orientation of the structural frame element, (eg. FE1 in FIGS. 3A and 3B), to which is pivotally affixed said elongated arm (EA), by said pivotal mounting (P). The orientation of said stage (STG) being effected by the action of gravity on the counter-weight (W), which is present at a lower end of said elongated arm (EA).

Figure 6:
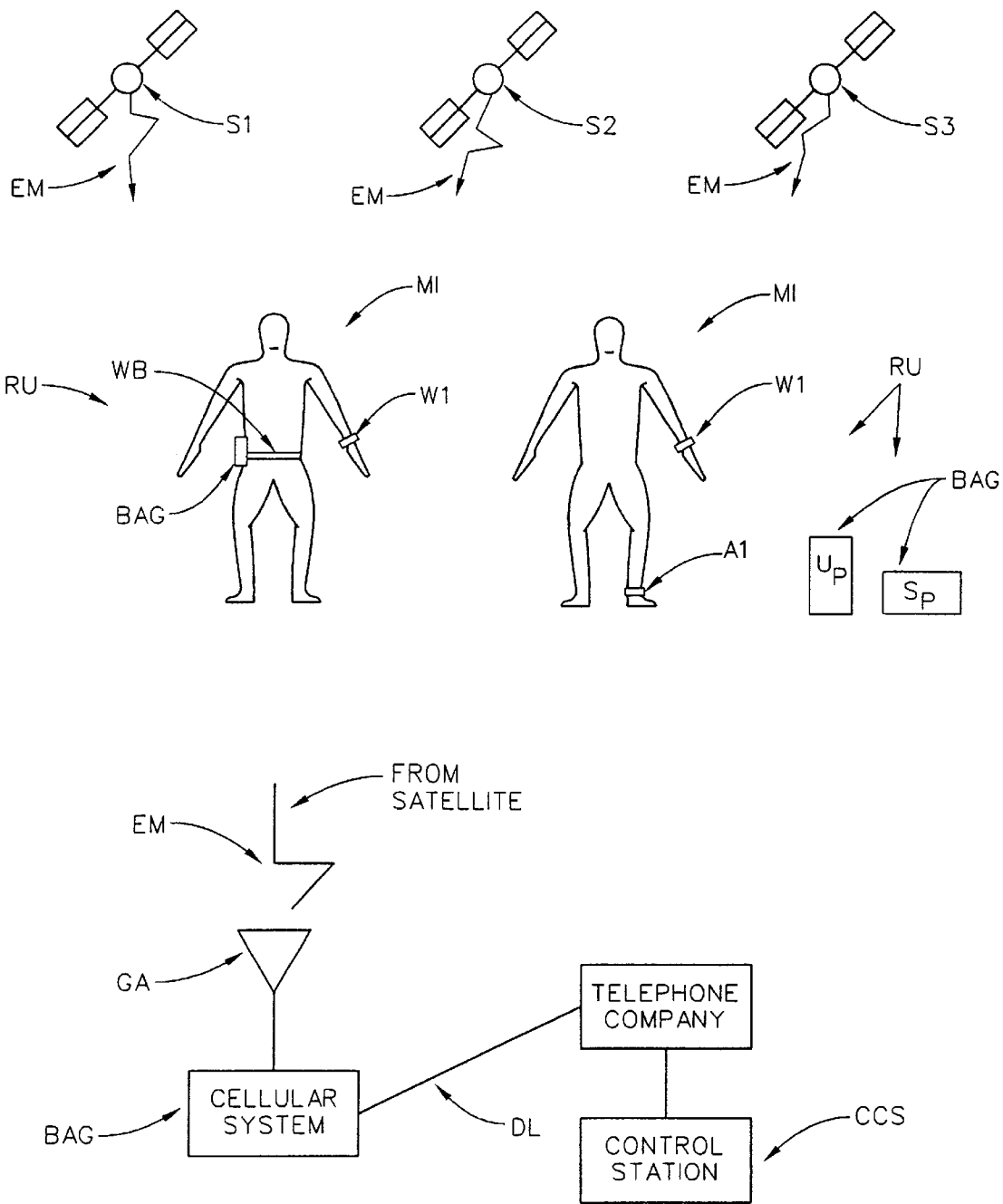
FIG. 6 shows an overall present invention system comprising a central control station (CCS) unit and a remote unit (RU), with indication of the presence of a global positioning system (GPS) operation and with indication of a monitored individual (MI).
Figure 7:
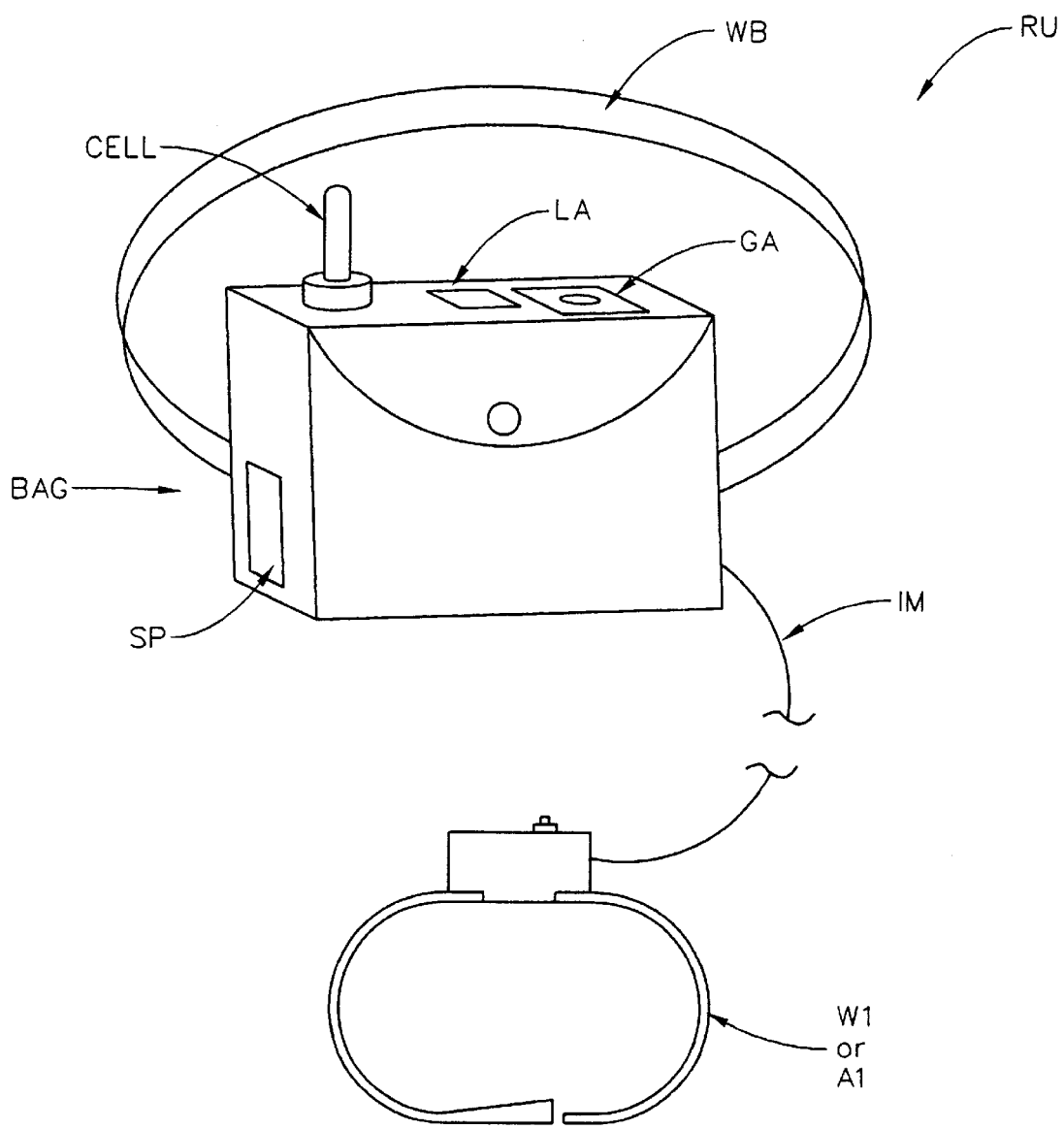
FIG. 7 shows the major elements of a present invention remote unit (RU), (eg. an individual mounted element (W1) (A1) and a remote unit (RU) element containing "Bag".
Figure 8:
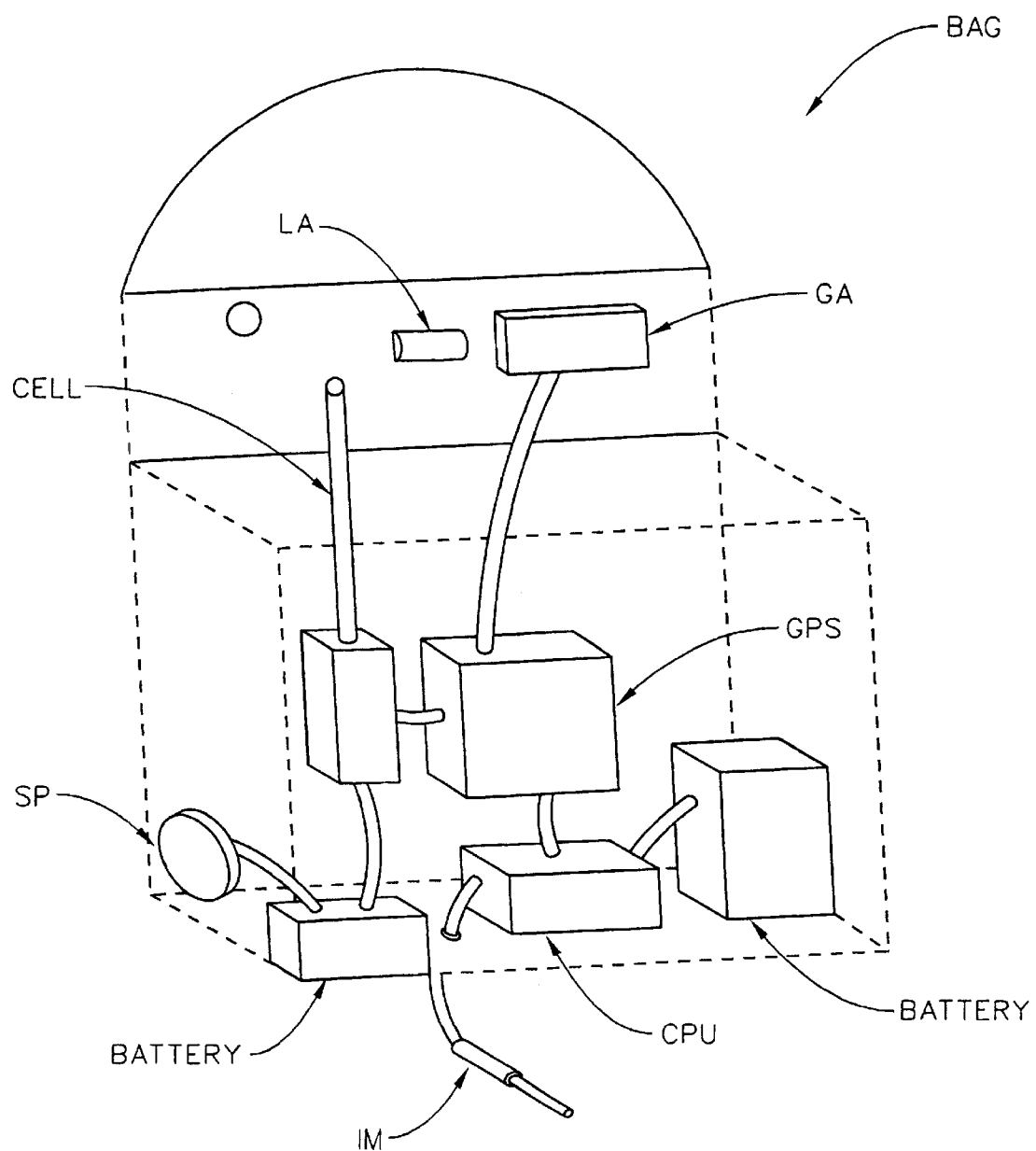
FIG. 8 shows more detail regarding elements present in the "BAG" of the present invention system remote unit (RU).

FIG. 6 shows an overall present invention system. Note that three earth orbiting satellites (S1) (S2) and (S3) are shown which send electromagnetic wave signals (EM) to the gimbal mounted antenna (GA) system which is mounted in a remote unit (RU) located "BAG" of the shown system for continuous electronic monitoring and tracking of monitored individual(s) from a central control station (CCS). Also shown is the central control station (CCS) which is demonstrated as receiving data from the "BAG" via telephone company "downlink" (DL) lines. Two indications of a monitored individual (MI) are shown. In one the "BAG" is secured thereto via a wasteband (WB), and in the other the "BAG" is positioned remote from the monitored individual. In the later case the "BAG" is shown in two positions, ($U_p$ and $S_p$), indicating that a "BAG" can be knocked-over in use. Shown also are demonstrative individual body worn wrist (W1) and ankle (A1) elements which in use communicate to the "BAG". Typically only one individual body worn element will be present. Continuing, FIG. 7 better shows said communication between an individual body worn element (W1) (A1) and a "BAG" is via an interconnection means (IM), which can be cable, fiber optics, ultrasound, or electromagnetic transmission. FIG. 7 further shows that a present invention remote unit (RU) is comprised of a "BAG", which "BAG" has present therein a speaker (SP), a lamp (LA), a cellular antenna (CELL) system and a gimbal mounted antenna (GA). FIG. 8 shows more detail of the elements present in a present invention "BAG". In addition to the elements shown in FIG. 7 there are shown Batteries, a central processing unit (CPU), and a global positioning system (GPS) means which receives signal from the gimbaled antenna system, (which provides electromagnetic signal reception means at an upper aspect thereof and identified as "Antenna" in FIGS. 3A, 3B and 5).

It is further noted that FIGS. 3A, 3B and 4 can be viewed as a remote unit (RU) "Bag" with a gimbal mounted antenna system present mounted therein.

With reference to FIGS. 6, 7 and 8 it can then be understood that a present invention system for continuous electronic monitoring and tracking of monitored individual(s) from a central control station (CCS) comprises one or more remote unit(s) (RU), each of said remote unit(s) (RU) has a "bag" which contains therein a global positioning system (GPS) means for determining the geographic position thereof at determined time(s) by use of electromagnetic wave signals received from at least one earth orbiting satellite. Said remote unit(s) each further comprise a programmable central processing unit (CPU) with accompanying memory storage which is connected to the position determining means, said central processing unit (CPU) being programmed to generate time stamps and accumulate time stamped remote unit (RU) position signal data at determined time intervals, and transmit said accumulated position signal and time stamped data to the central control station (CCS) via a downlink (DL). Said remote unit(s) each further comprise downlink (DL) communication means connected to the programmable central processing unit (CPU) so as to enable transmitting data from the remote unit (RU) to the central control station (CCS) and further enabling the receiving of data from the central control station (CCS) and providing said data to the central processing unit (CPU). Said remote unit(s) each have a monitored individual body worn element (W1) (A1) which, in use, communicates its presence to said "Bag" contained programmable central processing unit (CPU). As shown in FIGS. 3A, 3B and 5, the gimbal mounted antenna system is comprised of electromagnetic signal receiving means affixed to a gimbaled stage, (STG) said gimbaled stage (STG) being affixed to an upper end of an elongated arm (EA) which has a counter-weight (W) affixed to a lower end thereof, said elongated arm (A) being pivotally mounted via a pivotal mounting means (P) to a "Bag" structural frame element, such that said "Bag" structural frame element can be rotated in an effective pendulum plane of said elongated arm (A) without affecting an essentially constant orientation of said antenna system electromagnetic signal reception means, (see relationship between FIGS. 3a and 3b). In use when said "Bag" structural frame element changes orientation in an effective pendulum plane of said elongated arm (A), said antenna system electromagnetic signal reception means (A) orientation is maintained thereby allowing continued reception of global positioning system (GPS) electromagnetic wave signals from at least one earth orbiting satellite (S1) (S2) (S3).

A method of keeping electromagnetic signal receiving means of an antenna system, for continuous electronic monitoring and tracking of monitored individual(s) from a central control station (CCS), oriented so as to receive signals from an earth orbiting satellite source of electromagnetic signals, comprising the steps of:

a. providing a present invention system for continuous electronic monitoring and tracking of monitored individual(s) from a central control station (CCS) comprises one or more remote unit(s) (RU), as just described;

b. orienting said antenna system electromagnetic signal receiving means appropriately to receive electromagnetic signals from at least one earth orbiting satellite source of electromagnetic signals; and c. causing said structural frame element to rotate in an effective pendulum plane of said elongated arm;

such that said counter-weight affixed to the lower end of said elongated arm is continuously attracted by gravity toward the earth with the result that, via rotation of said elongated arm about said pivotal mounting to said structural frame element with respect to said structural frame element, the orientation of said antenna system electromagnetic signal receiving means present on the upper end of said gimbaled stage remains essentially constant while said structural frame element is caused to be so rotated.

Said method of keeping electromagnetic signal receiving means of an antenna system oriented so as to receive signals from a source of electromagnetic signals can include, in the step of orienting said antenna system electromagnetic signal receiving means appropriately to receive electromagnetic signals from an orbiting earth satellite involves a selection from the group consisting of:

a. continuously maintaining an essentially flat patch antenna system electromagnetic signal reception surface means in a plane which is essentially orthogonal to the vector direction of the force of gravity; and b. continuously maintaining an elongated dimension projection direction of a whip or helical antenna system electromagnetic signal reception means oriented essentially parallel to the vector direction of the force of gravity or, alternatively stated, along a radius which projects from the center of the earth outward toward the position of an electromagnetic signal transmitting earth orbiting satellite, said radius intersecting the surface of an idealized spherical model of the earth at a ninety degree angle.

Having hereby disclosed the subject matter of the present invention, it should be obvious that many modifications, substitutions, and variations of the present invention are possible in view of the teachings. It is therefore to be understood that the invention may be practiced other than as specifically described, and should be limited In its breadth and scope only by the Claims.

I claim:

1. A gimbal mounted antenna system in functional combination with a remote unit of a system for continuous electronic monitoring and tracking of monitored individuals from a central control station CCS;

said system for continuous electronic monitoring and tracking of monitored individuals from a central control station CCS comprising one or more remote units RU, each said remote unit RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, each said remote unit non-body worn bag further comprising a programmable central processing unit CPU with accompanying memory storage which is connected to the position determining means, said central processing unit CPU being programmed to generate time stamps and accumulate time stamped remote unit RU position signal data at determined time intervals, and transmit said accumulated position signal and time stamped data to the central control station CCS via a downlink; each said remote unit each further comprising communication means connected to the programmable central processing unit CPU so as to enable transmitting data from the remote unit RU to the central control station CS and further enabling the receiving of data from the central control station CCS and providing said data to the central processing unit CPU;

each said remote unit RU further comprising a monitored individual body worn element which, in use, communicates its presence to said non-body worn bag contained programmable central processing unit CPU;

said gimbal mounted antenna system being comprised of electromagnetic signal reception means affixed to a gimbaled stage, said gimbaled stage being affixed to an upper end of an elongated arm which has a counterweight affixed to a lower end thereof, said elongated arm being pivotally mounted to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained thereby allowing continued reception of global positioning system GPS electromagnetic wave signals from at least one earth orbiting satellite.

2. A gimbal mounted antenna system in functional combination with a remote unit of a system for continuous electronic monitoring and tracking of monitored individuals from a central control station CCS as in claim 1, wherein said central processing unit CPU is programmed to initiate an alarm if at least one of the members of the group consisting of:

loss of communication between said body worn element and said non-body worn bag contained programmable central processing unit CPU; and loss of electromagnetic signal reception by said antenna system electromagnetic signal reception means; occurs.

3. A gimbal mounted antenna system in functional combination with a remote unit of a system for continuous electronic monitoring and tracking of monitored individuals from a central control station CCS as in claim 1, wherein communication between said body worn element and said non-body worn bag contained programmable central processing unit CPU in a remote unit RU is by a means selected from the group consisting of:

cable;

fiber optics;

ultrasound; and electromagnetic transmission.

4. A gimbal mounted antenna system in functional combination with a remote unit of a system for continuous electronic monitoring and tracking of monitored individuals from a central control station CCS as in claim 1, wherein the body worn element is present on a selection from the group consisting of:

said monitored individual's wrist;

said monitored individual's ankle.

5. A method of keeping electromagnetic signal reception means of an antenna system, in a system for continuous electronic monitoring and tracking of monitored individuals from a central control station CCS, oriented so as to receive signals from an earth orbiting satellite source of electromagnetic signals, comprising the steps of:

a. providing a system for continuous electronic monitoring and tracking of monitored individuals from a central control station CCS comprising one or more remote units RU, each of said remote units RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, each said remote unit non-body worn bag further comprising a programmable central processing unit CPU with accompanying memory storage which is connected to the position determining means, said central processing unit CPU being programmed to generate time stamps and accumulate time stamped remote unit RU position signal data at determined time intervals, and transmit said accumulated position signal and time stamped data to the central control station CCS via a downlink; said remote units each further comprising communication means connected to the programmable central processing unit CPU so as to enable transmitting data from the remote unit RU to the central control station CCS and further enabling the receiving of data from the central control station CCS and providing said data to the central processing unit CPU;

each said remote unit RU further comprising a monitored individual body worn element which, in use, communicates its presence to said non-body worn bag contained programmable central processing unit CPU;

said gimbal mounted antenna system being comprised of electromagnetic signal reception means affixed to a gimbaled stage, said gimbaled stage being affixed to an upper end of an elongated arm which has a counter-weight affixed to a lower end thereof, said elongated arm being pivotally mounted to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained thereby allowing continued reception of global positioning system GPS electromagnetic wave signals from at least one earth orbiting satellite;

b. while causing said body worn element to communicate its presence to said non-body worn bag contained programmable central processing unit CPU, orienting said antenna system electromagnetic signal reception means appropriately to receive electromagnetic signals from at least one earth orbiting satellite source of electromagnetic signals; and c. causing said structural frame element to rotate; such that said counter-weight affixed to the lower end of said elongated arm is continuously attracted by gravity toward the earth with the result that, via rotation of said elongated arm about said pivotal mounting to said structural frame element with respect to said structural frame element, the orientation of said antenna system electromagnetic signal reception means present on the upper end of said gimbaled stage remains essentially constant while said structural frame element is caused to be so rotated.

6. A method of keeping electromagnetic signal reception means of an antenna system, in a system for continuous electronic monitoring and tracking of monitored individuals from a central control station CCS, oriented so as to receive signals from a source of electromagnetic signals as in claim 5, in which the step of orienting said antenna system electromagnetic signal reception means appropriately to receive electromagnetic signals from an orbiting earth satellite involves a selection from the group consisting of:

a. continuously maintaining an essentially flat patch antenna system electromagnetic signal reception surface means in a plane which is essentially orthogonal to the vector direction of the force of gravity; and b. continuously maintaining an elongated dimension projection direction of a whip or helical antenna system electromagnetic signal reception means oriented essentially parallel to the vector direction of the force of gravity or, alternatively stated, along a radius which projects from the center of the earth outward toward the position of an electromagnetic signal transmitting earth orbiting satellite, said radius intersecting the surface of an idealized spherical model of the earth at a ninety degree angle.

7. A gimbal mounted antenna system in functional combination with a remote unit of a system for continuous electronic monitoring and tracking of monitored individuals from a central control station CCS;

said system for continuous electronic monitoring and tracking of monitored individuals from a central control station CCS comprising one or more remote units RU, each of said remote units RU comprising a non-body worn bag, said non-body worn bag comprising a housing with a plurality of sides and a structural frame element, which non-body worn bag contains therein a programmable central processing unit CPU and a global positioning system GPS means for determining the geographic position thereof at determined times by use of electromagnetic wave signals received from at least one earth orbiting satellite;

each said remote unit RU further comprising a monitored individual body worn element which, in use, communicates its presence to said non-body worn bag contained programmable central processing unit CPU;

said gimbal mounted antenna system being comprised of electromagnetic signal reception means affixed to a gimbaled stage, said gimbaled stage being affixed to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained essentially unchanged, thereby allowing continued reception of global positioning system GPS electromagnetic wave signals from at least one earth orbiting satellite.

8. A gimbal mounted antenna system in functional combination with a remote unit of a system for continuous electronic monitoring and tracking of monitored individuals from a central control station CCS as in claim 7, wherein said central processing unit CPU is programmed to initiate an alarm if at least one of the members of the group consisting of:

loss of communication between said body worn element and said non-body worn bag contained programmable central processing unit CPU; and loss of electromagnetic signal reception by said antenna system electromagnetic signal reception means;

occurs.

9. A gimbal mounted antenna system in functional combination with a remote unit of a system for continuous electronic monitoring and tracking of monitored individuals from a central control station CCS as in claim 7, wherein communication between said body worn element and said non-body worn bag contained programmable central processing unit CPU is by a means selected from the group consisting of:

cable;
fiber optics;
ultrasound; and
electromagnetic transmission.

10. A gimbal mounted antenna system in functional combination with a remote unit of a system for continuous electronic monitoring and tracking of monitored individuals from a central control station CCS as in claim 7, wherein the body worn element is present on a selection from the group consisting of:
said monitored individual's wrist;
said monitored individual's ankle.

11. A method of keeping electromagnetic signal reception means of an antenna system, in a system for continuous electronic monitoring and tracking of monitored individuals from a central control station CCS, oriented so as to receive signals from an earth orbiting satellite source of electromagnetic signals, comprising the steps of:

a. providing a system for continuous electronic monitoring and tracking of monitored individuals from a central control station CCS comprising one or more remote units RU, each of said remote units RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, and a central processing unit CPU for processing information;

each said remote unit RU further comprising a monitored individual body worn element which, in use, communicates its presence to said non-body worn bag contained programmable central processing unit CPU;

said system for continuous electronic monitoring and tracking of monitored individuals further comprising at least one gimbal mounted antenna system comprised of electromagnetic signal reception means affixed to a gimbaled stage, said gimbaled stage being affixed to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained essentially unchanged, thereby allowing continued reception of global positioning system GPS electromagnetic wave signals from at least one earth orbiting satellite;

b. while causing said body worn element to communicate its presence to said non-body worn bag contained programmable central processing unit CPU, orienting said gimbal mounted antenna system electromagnetic signal reception means appropriately to receive electromagnetic signals from at least one earth orbiting satellite source of electromagnetic signals; and c. causing said structural frame element to rotate; such that, via operation of said gimbal mounted antenna system, the orientation of said antenna system electromagnetic signal reception means remains essentially constant.

12. A method of keeping electromagnetic signal reception means of an antenna system, in a system for continuous electronic monitoring and tracking of monitored individuals from a central control station CCS, oriented so as to receive signals from a source of electromagnetic signals as in claim 11, in which the step of orienting said antenna system electromagnetic signal reception means appropriately to receive electromagnetic signals from an orbiting earth satellite involves a selection from the group consisting of:

a. continuously maintaining an essentially flat patch antenna system electromagnetic signal reception surface means in a plane which is essentially orthogonal to the vector direction of the force of gravity; and b. continuously maintaining an elongated dimension projection direction of a whip or helical antenna system electromagnetic signal reception means oriented essentially parallel to the vector direction of the force of gravity or, alternatively stated, along a radius which projects from the center of the earth outward toward the position of an electromagnetic signal transmitting earth orbiting satellite, said radius intersecting the surface of an idealized spherical model of the earth at a ninety degree angle.

13. A gimbal mounted antenna system in functional combination with a remote unit of a system for continuous electronic monitoring and tracking of a monitored individual from a central control station CCS;

said system for continuous electronic monitoring and tracking of a monitored individual from a central control station CCS comprising a remote unit RU, said remote unit RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, said remote unit non-body worn bag further comprising a programmable central processing unit CPU with accompanying memory storage which is connected to the position determining means, said central processing unit CPU being programmed to generate time stamps and accumulate time stamped remote unit RU position signal data at determined time intervals, and transmit said accumulated position signal and time stamped data to the central control station CCS via a downlink; said remote unit further comprising communication means connected to the programmable central processing unit CPU so as to enable transmitting data from the remote unit RU to the central control station CCS and further enabling the receiving of data from the central control station CCS and providing said data to the central processing unit CPU;

said remote unit RU further comprising a monitored individual body worn element which, in use, communicates its presence to said non-body worn bag contained programmable central processing unit CPU;

said gimbal mounted antenna system being comprised of electromagnetic signal reception means present at an upper end of an elongated arm, which elongated arm has a counter-weight affixed to a lower end thereof, said elongated arm being pivotally mounted to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained thereby allowing continued reception of global positioning system GPS electromagnetic wave signals from at least one earth orbiting satellite.

14. At least one gimbal mounted antenna system in functional combination with a remote unit of a system for continuous electronic monitoring and tracking of a monitored individual from a central control station CCS;

said system for continuous electronic monitoring and tracking of a monitored individual from a central control station CCS comprising a remote unit RU, said remote unit RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, said remote unit non-body worn bag further comprising a programmable central processing unit CPU with accompanying memory storage which is connected to the position determining means, said central processing unit CPU being programmed to generate time stamps and accumulate time stamped remote unit RU position signal data at determined time intervals, and transmit said accumulated position signal and time stamped data to the central control station CCS via a downlink; said remote unit further comprising communication means connected to the programmable central processing unit CPU so as to enable transmitting data from the remote unit RU to the central control station CCS and further enabling the receiving of data from the central control station CCS and providing said data to the central processing unit CPU;

said remote unit RU further comprising a monitored individual body worn element which, in use, communicates its presence to said non-body worn bag contained programmable central processing unit CPU;

said at least one gimbal mounted antenna system being comprised of electromagnetic signal reception means present at an upper end of an elongated arm, which elongated arm has a counter-weight affixed to a lower end thereof, said elongated arm being pivotally mounted to said non-body worn bag structural frame element, such that said non-body worn bag structural frame element can be rotated without affecting an essentially constant orientation of said antenna system electromagnetic signal reception means;

such that in use when said non-body worn bag structural frame element changes orientation, said antenna system electromagnetic signal reception means orientation is maintained thereby allowing continued reception of global positioning system GPS electromagnetic wave signals from at least one earth orbiting satellite.

15. At least one gimbal mounted antenna system in functional combination with a remote unit of a system for continuous electronic monitoring and tracking of a monitored individual from a central control station CCS as in claim 14, in which there are present at least first and second gimbal mounted antenna systems, each thereof being comprised of electromagnetic signal reception means present at one end of an elongated arm, and each said elongated arm having a counter-weight affixed to the other end thereof, said elongated arms being pivotally mounted to said non-body worn bag structural frame element, such that when said first end of one of the elongated arms is oriented upward, said non-body worn bag structural frame element can be rotated without affecting an essentially constant upward orientation of the antenna system electromagnetic signal reception means associated therewith;

said first gimbal mounted antenna system being mounted to a first of said non-body worn bag housing plurality of sides, and said second gimbal mounted antenna system being mounted to a second of said non-body worn bag housing plurality of sides.

16. At least two antenna system electromagnetic signal reception means in functional combination with a remote unit of a system for continuous electronic monitoring and tracking of a monitored individual from a central control station CCS;

said system for continuous electronic monitoring and tracking of a monitored individual from a central control station CCS comprising a remote unit RU, said remote unit RU comprising a non-body worn bag, said non-body worn bag comprising a housing with a plurality of sides and a structural frame element, which non-body worn bag contains therein a global positioning system GPS means for determining the geographic position thereof at determined times by use of electromagnetic wave signals received from at least one earth orbiting satellite, said remote unit non-body worn bag further comprising a programmable central processing unit CPU with accompanying memory storage which is connected to the position determining means, said central processing unit CPU being programmed to generate time stamps and accumulate time stamped remote unit RU position signal data at determined time intervals, and transmit said accumulated position signal and time stamped data to the central control station CCS via a downlink; said remote unit further comprising communication means connected to the programmable central processing unit CPU so as to enable transmitting data from the remote unit RU to the central control station CCS and further enabling the receiving of data from the central control station CCS and providing said data to the central processing unit CPU;

said remote unit RU further comprising a monitored individual body worn element which, in use, communicates its presence to said non-body worn bag contained programmable central processing unit CPU;

at least two of said at least two antenna system electromagnetic signal reception means being present on different sides of the plurality of sides of said non-body worn bag housing, such that the structural frame element thereof can be rotated about at least one axis with at least one of said antenna system electromagnetic signal reception means maintaining signal reception contact with at least one earth orbiting satellite;

such that in use when said non-body worn bag structural frame element changes orientation about said at least one axis, reception of global positioning system GPS electromagnetic wave signals from at least one earth orbiting satellite is maintained.

* * * * *